United States Patent [19]
Ashe

[11] 4,029,964
[45] June 14, 1977

[54] DETECTOR CONSTRUCTION FOR A SCINTILLATION CAMERA

[75] Inventor: John B. Ashe, Palatine, Ill.

[73] Assignee: G. D. Searle & Co., Skokie, Ill.

[22] Filed: Aug. 11, 1975

[21] Appl. No.: 603,377

[52] U.S. Cl. .............................. 250/368; 250/363 S
[51] Int. Cl.² .......................................... G01T 1/20
[58] Field of Search ............... 250/363 S, 367, 368, 250/361

[56] References Cited
UNITED STATES PATENTS

| | | | |
|---|---|---|---|
| 3,908,128 | 9/1975 | Richey | 250/363 S |
| 3,919,556 | 11/1975 | Berninger | 250/363 S |

Primary Examiner—Archie R. Borchelt
Attorney, Agent, or Firm—Dennis O. Kraft; Walter C. Ramm; Albert Tockman

[57] ABSTRACT

An improved transducer construction for a scintillation camera in which a light conducting element is equipped with a layer of moisture impervious material. A scintillation crystal is thereafter positioned in optical communication with the moisture impervious layer and the remaining surfaces of the scintillation crystal are encompassed by a moisture shield. Affixing the moisture impervious layer to the light conducting element prior to attachment of the scintillation crystal reduces the requirement for mechanical strength in the moisture impervious layer and thereby allows a layer of reduced thickness to be utilized. Preferably, photodetectors are also positioned in optical communication with the light conducting element prior to positioning the scintillation crystal in contact with the impervious layer.

13 Claims, 4 Drawing Figures

DETECTOR CONSTRUCTION FOR A SCINTILLATION CAMERA

The present invention discloses an improved construction of a transducer for a scintillation camera. The unique construction is achieved through a novel method of assembly of component elements of the scintillation camera transducer.

BACKGROUND OF THE INVENTION

Scintillation cameras are widely used in the field of nuclear medicine for detecting lesions, cancerous growths, circulatory irregularities, and other abnormalities in the internal organs of a living subject. The basic scintillation camera is described in U.S. Pat. No. 3,011,057. In the operation of a scintillation camera, a patient is injected with a small quantity of a radioactive substance having an affinity for a particular organ or area of interest within the body of a living subject. The detector element of the scintillation camera, which includes a radiation transducer, is positioned adjacent to the area of the patients's body to be examined. Gamma rays produced by the radioactive disintegrations of the radioisotope administered pass from within the body of the patient to strike a planar scintillation crystal. In response to the impinging gamma rays, the scintillation crystal emits flashes of light. An array of photodetectors viewing the scintillation crystal responds to the light flashes for each detected radioactive event by generating electrical impulses. Each photodetector views an overlapping portion of the scintillation crystal. The strength of the electrical impulses from each photodetector may be directly related to the distance of the scintillation in the crystal from that photodetector. In this manner, the coordinates of interaction of gamma rays with the scintillation crystal in a two-dimensional coordinate system may be determined. By interposing a collimator between the scintillation crystal and the patient, the points of origin of the detected gamma rays within the body of the patient may be ascertained in the same two-dimensional coordinate system.

In conventional scintillation cameras, the detector construction involves the incorporation of a scintillation crystal subassembly. This subassembly includes a scintillation crystal of thallium-activated sodium iodide. The scintillation crystal is in the form of a disc with one face of the disc positioned in contact with a glass window, one-half inch in thickness formed of pyrex 7740 glass. This glass window is an optical window which permits scintillations to escape the sodium iodide and impinge upon the photodetectors. The remaining surfaces of the scintillaton crystal are surrounded by an aluminum casing which is sealed to the glass window thereby entrapping the sodium-iodide crystal in a moisture free environment. This protection from moisture is necessary because sodium iodide is hygroscopic, and when moisture is absorbed by the sodium iodide crystal, the crystal becomes cloudy and unsuitable for use as a scintillation crystal in a scintillation camera.

The conventional use of the one-half inch thick glass plate represents a compromise among several requirements for a scintillation camera. The relatively large thickness of the glass window has heretofore been required to protect the sodium iodide crystal from mechanical stress during the assembly of the scintillation camera detector head. In the conventional manner of assembly, an optical coupling compound is coated either on the surface of the glass window or on a light conducting element sometimes referred to as a "light pipe". The scintillation detector subassembly and the light conducting element are then forced together with considerable mechanical pressure to obtain complete optical coupling between the light conducting element and the scintillation crystal. Later during the assembly process, and after the light conducting element has been coupled to the scintillation crystal subassembly, photodetectors are similarly positioned in optical contact with the light conducting element to form an array as previously described. Again, mechanical force is required to ensure a complete and uniform optical coupling between the photodetectors and the light conducting element.

In the conventional assembly of scintillation camera detectors, it has been found that if the glass window associated with the scintillation crystal subassembly is less than about one-half inch in thickness, flexing of the glass window occurs during optical coupling of a light conducting element and during coupling of the photodetectors to the extent that too much stress is placed on the sodium iodide crystal, and the crystal is likely to fracture. If this occurs, of course, the scintillation crystal is useless and must be replaced at considerable expense.

The relatively thick glass window used in conventional scintillation cameras has always been considered undesirable because it absorbs a significant portion of the light transmitted from the scintillation crystal. This light absorption is particularly severe for light traversing the glass window at angles other than at a path perpendicular to the glass window. The result is a degradation of resolution of the instrument. Alternatives have been sought to remedy the design shortcomings inherent in the relatively thick glass window of conventional commercial scintillation detectors. One alternative has been a one-half inch thick quartz window in place of the glass window. Quartz has a superior index of transmission of light from the sodium iodide crystal, but it also has a worse match of refractive index with sodium iodide than does the current glass window. This mismatch of refractive indices produces errors in the positional information transmitted by the photodetectors. Crown glass has also been considered as an alternative to the pyrex glass conventionally used. However, because of the need for mechanical rigidity, no major reduction in window thickness has been practical using this alternative.

SUMMARY OF THE INVENTION

It is an object of the present invention to provide a construction of a scintillation detector for a gamma camera in which the transparent window adjacent to the scintillation crystal is much thinner than the corresponding window in conventional scintillation camera detectors, but which still provides the necessary moisture barrier and which does not expose a hygroscopic scintillation crystal to harmful mechanical stress.

It is a further object of the present invention to provide a window for coupling to a sodium iodide crystal in a scintillation camera which absorbs significantly less light from the scintillation crystal than is absorbed in conventional gamma cameras. This reduction in absorption is made possible by the reduced window thickness.

Another object of the invention is to expose the scintillation crystal to an absolute minimum of mechanical stress. This is achieved by positioning the scintillation crystal in contact with the transparent window of reduced thickness only after that window has been optically coupled to the light conducting element or "light pipe". Moreover, the scintillation crystal is preferably positioned even after the photodetectors have likewise been optically coupled to the light conducting element.

A further object of the invention is to expand the scope of materials from which the optical coupling compound may be selected to join conducting element and the window against which the scintillation crystal is thereafter positioned. By coupling the light conducting element to the window in the absence of the scintillation crystal, heat setting or catalytic setting compounds can be used as the optical coupling media with no regard for heat damage to the sodium iodide crystal. This danger has heretofore precluded the use of heat-setting plastics or silicone rubber substances which have superior optical properties when compared to the conventional optical coupling compound used for this purpose. Such heat setting or catalytic setting compounds have a stability of longer duration in the scintillation camera since the coupling need not be a fluid and can be restricted from flowing out of the joint between the transparent window and the light conducting element.

Another object of the invention is to reduce to an absolute minimum the thickness of the moisture barrier formed by the window in contact with the scintillation crystal. A moisture barrier is necessary because the materials having the best optical properties for use as light conducting elements are also somewhat porous to moisture. For this reason, unless a moisture barrier is utilized, the sodium iodide crystal will become discolored by virtue of moisture penetration through the optical coupling element. However, is one form of the invention, a thin coating of a plastic in liquid form may be applied directly onto a planar surface of a laminar transparent light conducting element. The plastic is cured to form a moisture impermeable transparent layer bonded to the light conducting element. This form of construction minimizes the window thickness required to protect the sodium iodide crystal from moisture, thereby also minimizing the amount of light absorption in such a window.

In one broad aspect this invention is, in a scintillation camera for radioisotope imaging employing a laminar scintillation crystal, an array of photodetectors in optical communication with said scintillation crystal for generating electrical signals providing position information with regard to the scintillations occurring in said scintillation crystal in reponse to incident gamma radiation wherein each photodetector views an overlapping portion of said scintillation crystal, a transparent light conducting element interposed between said scintillation crystal and said array of photodetectors, electrical circuitry connected to said photodetectors for receiving the aforesaid electrical signals from said photodetectors and for producing composite image signals, and an image representation means for receiving said image signals and depicting signals for a single detected radioactive event as positional coordinates of the interaction of said event with the aforesaid crystal, the improvement comprising a laminar impermeable barrier less than one-quarter inch in thickness interposed between said scintillation crystal and said light conducting element.

In another aspect this invention may be considered to be, in a method of manufacturing a radiation transducer for a scintillation camera employing a hygroscopic scintillation crystal, the improvement comprising the steps of joining one surface of a transparent laminar bilateral impermeable sheet less than one-quarter inch in thickness to a light conducting element of substantially greater thickness by means of a thermally sealable optical coupling compound, sealing said compound to provide a solid phase optical interface, and thereafter securing a planar scintillation crystal in contact with the other surface of said transparent sheet.

Alternatively, another practice of the method of this invention may comprise the steps of applying in a liquid form a thin coating of a plastic onto a planar surface of a laminar transparent light conducting element, curing said plastic to form a moisture impermeable transparent layer bonded to said light conducting element, securing a planar scintillation crystal with one surface in contact with said transparent layer, and enveloping the remaining surfaces of said scintillation crystal in a moisture-proof shield.

BRIEF DESCRIPTION OF THE INVENTION

The invention may be more clearly illustrated in the accompanying drawings in which FIG. 1 is an elevational view of a scintillation camera;

DETAILED DESCRIPTION

Figure 1:
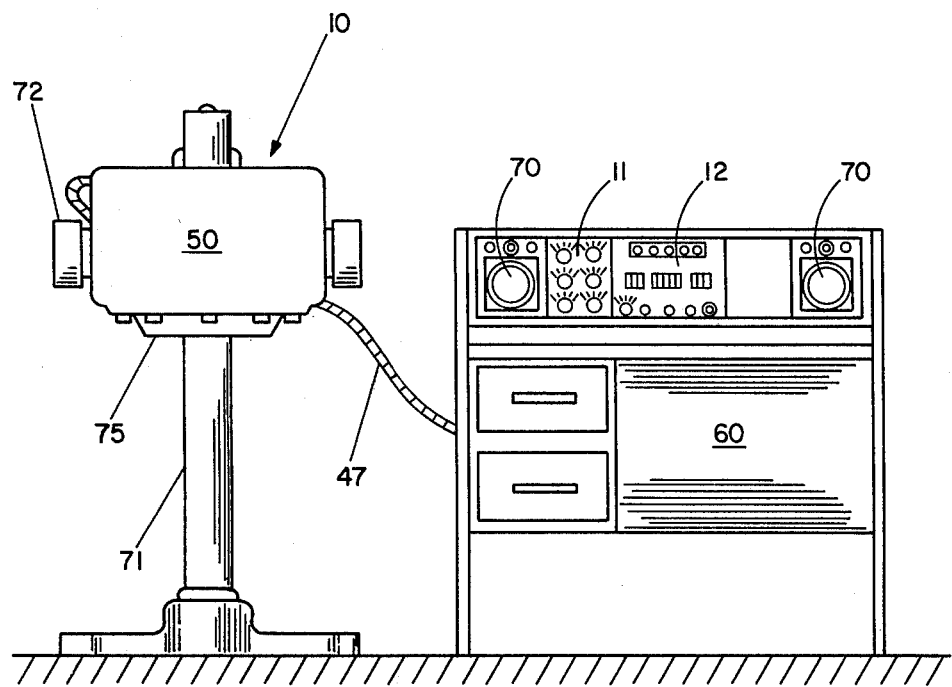
Figure 2:
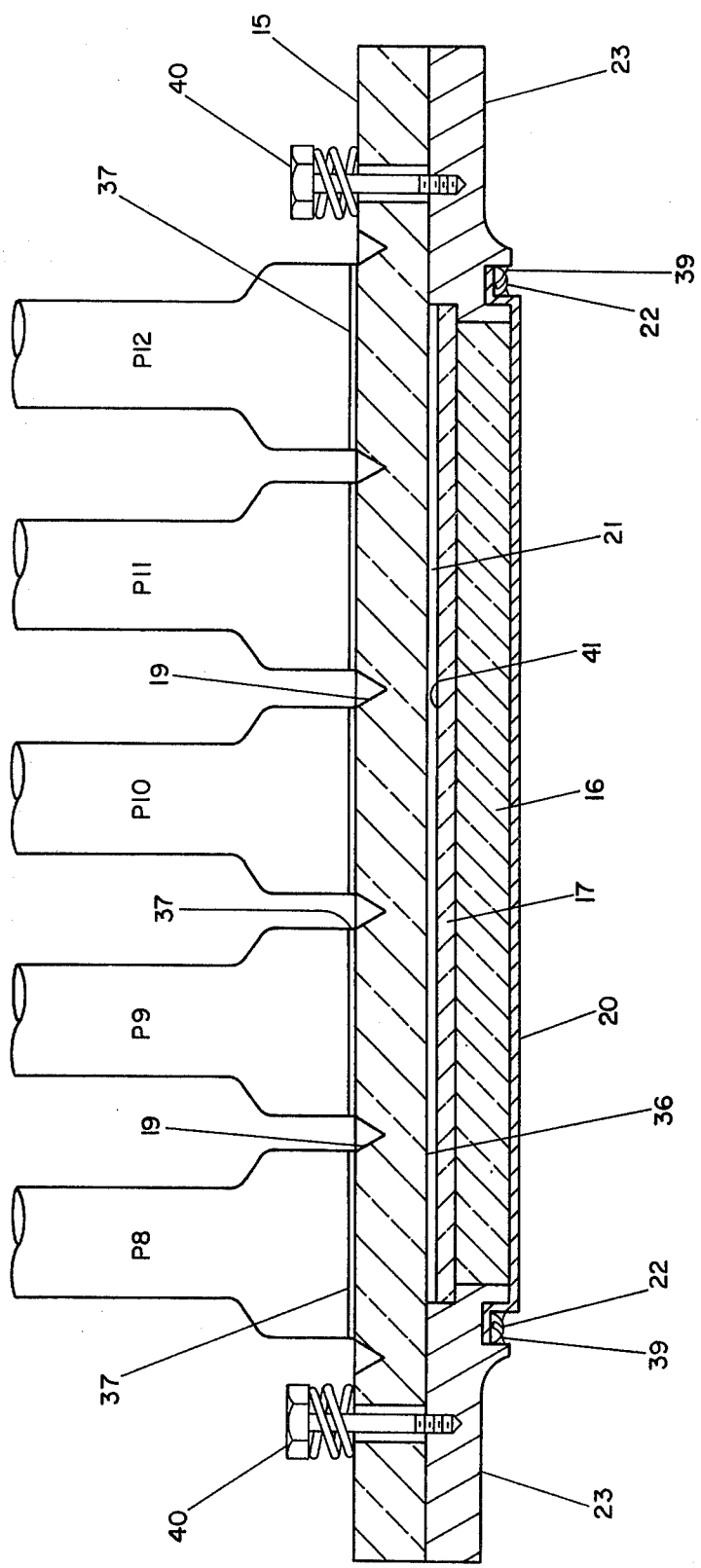
FIG. 2 is an enlarged sectional view of a portion of the scintillation camera detector system employing one embodiment of this invention.

Referring now to FIG. 1 there is illustrated a scintillation camera for radioisotope imaging including a console portion 60 and a detector portion 10. The detector portion 10 includes a detector head 50 supported in the arms of a yoke 72 mounted on an upright column 71. A collimator 75 is typically mounted on the face of the detector head 50 as illustrated. Detector head 50 is connected to the console by means of a cable harness 47. The detector console 60 includes dual cathode ray oscilloscopes 70 which form image representation means for receiving electrical image signals and for depicting such signals for a single detected radioactive event as positional coordinates of interaction of the event with a scintillation crystal in the detector head 50. The detector console 60 also includes a control panel 11, an indicator panel 12, and position computation circuitry for receiving electrical signals from photodetectors in the detector head 50 for producing composite image signals for transmission to the cathode ray oscilloscopes 70. Referring now to FIG. 2, there are illustrated in a sectional view five photomultiplier tubes P8, P9, P10, P11, and P12. These photomultiplier tubes form only part of a hexagonal array of a total of nineteen photodetectors, all of which are in optical communication with overlapping portions of a thallium-activated sodium iodide scintillation crystal 16. The geometry of this arrangement is illustrated in more detail in U.S. Pat. No. 3,723,735, but any conventional photomultiplier configuration can be employed. The photodetectors generate electrical signals which provide positional information with regard to scintillations occurring in the scintillation crystal 16 in response to incident gamma radiation. A more detailed explanation of the position determination is provided in U.S. Pat. Nos. 3,732,419 and 3,723,735, but such a detailed explanation is not necessary for purposes of the present invention.

The detector assembly also includes a transparent laminar light conducting element 15 which has a planar surface 36. The opposing surface is comprised of a plurality of platforms, one to accommodate each photomultiplier tube. A number of V-shaped indentations 19 encircle the photodetector platforms and aid in channeling light flashes from scintillations in the scintillation crystal 16 into the photomultiplier tube nearest the scintillation. These indentations 19 also assist in reducing the amount of light transmitted to the more distant photomultiplier tubes. In FIG. 2, a window is provided between the scintillation crystal 16 and the light conducting element 15. This window takes the form of a bilateral glass covered disc 17 and forms a laminar impermeable barrier and, by virtue of the present invention, is less than one-quarter inch in thickness, preferably no greater than about one-eighth of an inch in thickness. A layer 21 of a thermally-cured optical coupling compound provides an interface between the glass moisture barrier 17 and the transparent light conducting element 15. This optical coupling compound may be formed of silicone rubber, though other thermally or catalytically cured substances might also be used. Conventional optical coupling compounds could be used, but the greatest advantage is obtained when the layer 21 is applied in a liquid or gel form and is thereafter cured. The principal requirements of the optical coupling compounds which maybe used are that they must be highly transparent to the light from the sodiumiodide crystal 16; that they have an index of refraction similar to that of the glass disc 17 and light pipe 15; and that they provide an unbroken area of contact between both the laminar impermeable sheet 17 and the planar surface 36 of the lucite light pipe 15.

Because the crystal 16 is hygroscopic, it must be completely encapsulated within moisture resistant materials. In addition to the moisture impermeable transparent glass sheet 17, there is provided an aluminum shield 20 fastened to a steel frame 23 by means of machine screws 22 which are embedded in a potting compound 39. The steel frame 23 and the aluminum shield 20 envelop the surfaces of the scintillation crystal 16, other than the surface in contact with the glass disc 17, within a moisture proof shield. Likewise, the glass disc 17 forms a moisture barrier so that the scintillation crystal 16 is protected from damage by water or water vapor. The steel frame 23 is held in place with respect to the lucite light pipe 15 by means of spring biased bolts 40.

Figure 3:
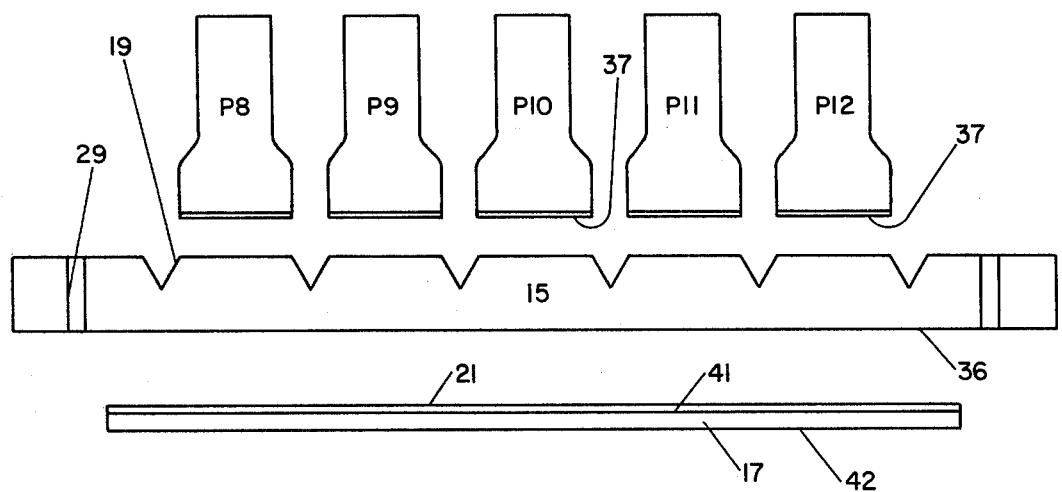
FIG. 3 illustrates the construction of the embodiment of FIG. 2.

In the manufacture of the portion of the scintillation detector of FIG. 2, as illustrated in FIG. 3, there is a departure from the conventional techniques of scintillation detector construction. According to the method of the present invention, a thermally sealable optical coupling compound, such as silicone rubber, is applied as a layer 21 on the transparent laminar impermeable sheet 17. Alternatively, the layer 21 might be applied to the surface 36 of the light conducting element 15. In either event, mechanical force is used to optically couple the surface 41 of the transparent laminar impermeable sheet 17 to the surface 36 of the light conducting element 15 with the layer 21 of the optical coupling compound interposed therebetween. Heat is applied to the structure to seal the optical coupling compound thereby joining the sheet 17 to the element 15 with a solid phase optical interface. Thereafter, a planar scintillation crystal (not shown) is brought into contact with the surface 42 of the transparent sheet 17 and the remainder of the moisture shielding constructed as aforesaid. Before the scintillation crystal is positioned adjacent to the sheet 17, however, the photodetectors are preferably first secured in optical communication with the light conducting element 15. This is achieved by coating the light sensitive faces of the photomultiplier tubes with an optical coupling compound 37. This optical coupling compound may be of a conventional type for preventing a large mismatch in the indices of refraction at the optical interface. Only after completion of the foregoing steps is the scintillation crystal brought into position. Thus, the scintillation crystal is not exposed to damaging mechanical stresses and thermal efforts.

Figure 4:
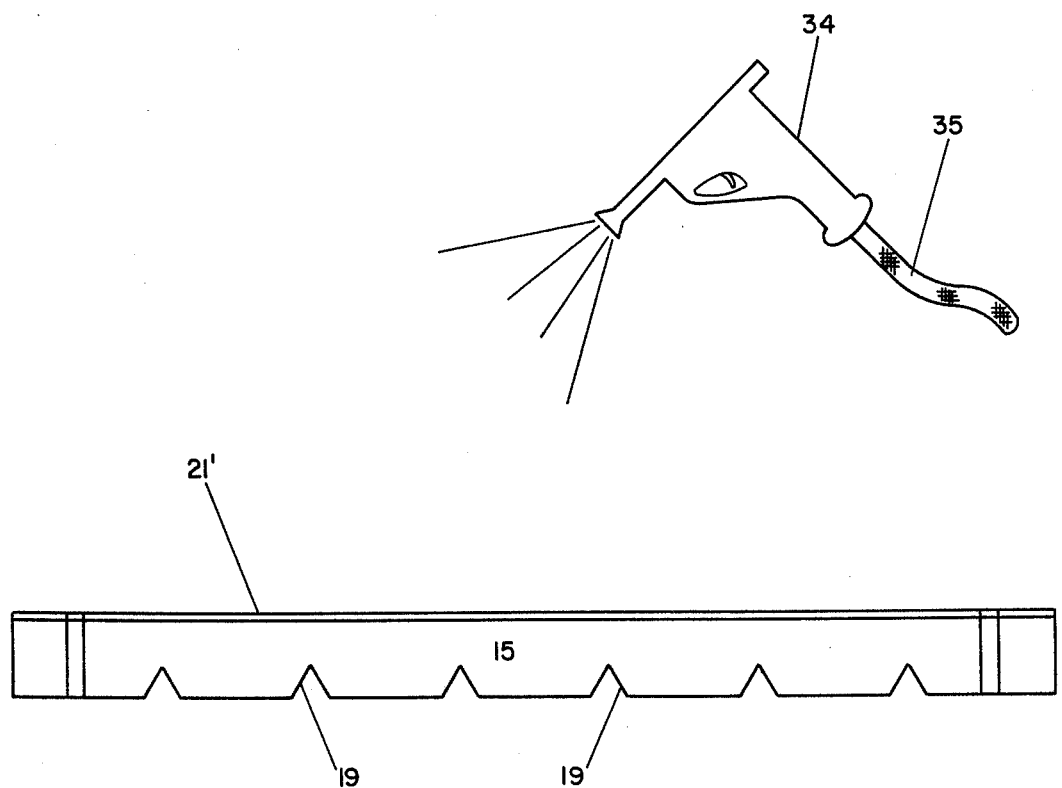
FIG. 4 illustrates an alternative method of manufacture of a scintillation camera according to the present invention.

In an alternative form of this invention, there is no requirement for an optical coupling compound between the moisture barrier 21' and the planar surface of the light conducting element 15. In this construction, and as is illustrated in FIG. 4, a thin coating of a plastic is applied in liquid form by means of a spray nozzle assembly 34 having a supply conduit 35. In this manner, a thin coating of plastic is sprayed onto the planar surface of the light conducting element 15 (inverted with respect to its position in FIG. 3) to form a coated layer 21' thereon. The coated light conducting element 15 is thereafter heated so that the coating layer 21' cures to form a moisture impermeable transparent layer bonded directly to the light conducting element 15. Satisfactory materials for use in creating the coating layer 21' include polyvinyl butral and polystyrene. It should be considered, however, that other transparent, water impermeable substances may be substituted therefor. While it is not absolutely necessary to solidify the layer 21', solidification aids in maintaining a uniform transparent layer on the planar surface of the light conducting element 15.

After the layer 21' has been created, a planar scintillation crystal (not shown) is brought into contact with the transparent layer 21'. The other surfaces of the scintillation crystal not in contact with the layer 21' are enveloped by a moisture proof shield in the manner previously described.

The foregoing illustrations of scintillation camera detector construction and assembly should not be considered as limiting, as various alternatives and modifications thereto will be readily apparent and will still fall within the scope of the invention as defined by the claims. For example, while discussion of the scintillation crystal employed in this invention has been limited to a crystal constructed of thallium-activated sodium iodide, since this is the material of choice in scintillation cameras, the advantages of the present invention are obtained in a scintillation camera employing any hygroscopic scintillation crystal.

I claim:

1. In a scintillation camera for radioisotope imaging employing a laminar scintillation crystal, an array of photodetectors in optical communication with said scintillation crystal for generating electrical signals providing position information with regard to scintillations occurring in said scintillation crystal in response to incident gamma radiation wherein each photodetector views an overlapping portion of said scintillation crystal, a transparent light conducting element interposed between said scintillation crystal and said array of photodetectors, electrical circuitry connected to said photodetectors for receiving the aforesaid electrical signals from said photodetectors and for producing composite image signals, and an image representation means for receiving said image signals and depicting signals for a single detected radioactive event as positional coordinates of interaction of said event with the aforesaid crystal, the improvement comprising a laminar moisture-impermeable barrier less than one quarter inch in thickness interposed between said scintillation crystal and said light conducting element.

2. The scintillation camera of claim 1 wherein said laminar moisture-impermeable barrier is comprised of a glass sheet.

3. The scintillation camera of claim 2 further comprising a layer of a thermally cured optical coupling compound providing an interface between said glass sheet and said transparent light conducting element.

4. The scintillation camera of claim 3 wherein said optical coupling compound comprises silicone rubber.

5. The scintillation camera of claim 2 wherein said laminar moisture-impermeable barrier is comprised of a plastic layer bonded to said light conducting element.

6. The scintillation camera of claim 5 wherein said plastic layer is polyvinyl butral.

7. The scintillation camera of claim 5 wherein said plastic is polystyrene.

8. In a method of manufacturing a radiation transducer for a scintillation camera employing a hygroscopic scintillation crystal, the improvement comprising the steps of joining one surface of a transparent laminar bilateral moisture-impermeable sheet less than one quarter inch in thickness to a light conducting element of substantially greater thickness by means of a thermally sealable optical coupling compound, sealing said compound to provide a solid phase optical interface, and thereafter securing a planar scintillation crystal in contact with the other surface of said transparent sheet.

9. The method of claim 8 further comprising the step of securing all required photodetectors in optical communication with said light conducting element prior to securing said planar scintillation crystal to said transparent sheet.

10. In a method of manufacturing a scintillation detector assembly for a gamma ray scintillation camera, the improvement comprising coupling a layer less than one quarter inch in thickness of a transparent moisture-impermeable material to a light guide adapted for positioning in contact with an array of photodetectors, and thereafter securing one surface of a crystal of thallium activated sodium iodide to said layer and encompassing the remaining surfaces of said sodium iodide crystal within a moisture proof shield.

11. In a method of manufacturing a radiation transducer for a scintillation camera employing a hygroscopic scintillation crystal, the improvement comprising the steps of applying in liquid form a thin coating of a plastic less than one quarter inch in thickness onto a planar surface of a laminar transparent light conducting element, curing said plastic to form a moisture-impermeable transparent layer bonded to said light conducting element, securing a planar scintillation crystal with one surface in contact with said transparent layer, and enveloping the remaining surfaces of said scintillation crystal in a moisture proof shield.

12. The method of claim 11 wherein said plastic is polyvinyl butral.

13. The method of claim 11 wherein said plastic is polystyrene.

* * * * *